United States Patent [19]

Caubere et al.

[11] Patent Number: 5,283,360
[45] Date of Patent: Feb. 1, 1994

[54] SELECTIVE EPOXIDATION OF UNSATURATED (METH)ACRYLATES, NEW FUNCTIONAL (METH)ACRYLATES, AND POLYMERS THEREOF

[75] Inventors: Paul Caubere, Nancy; Yves Fort, Vandoeuvre les Nancy; Agnès Ortar, Jarny, all of France

[73] Assignee: Atochem, Paris la Defense, France

[21] Appl. No.: 725,318

[22] Filed: Jul. 8, 1991

[30] Foreign Application Priority Data

Jul. 6, 1990 [FR] France ................. 90 08607

[51] Int. Cl.$^5$ ............................. C07C 69/52
[52] U.S. Cl. ................... 560/220; 560/224; 558/250; 564/208
[58] Field of Search ........... 560/220, 224; 558/250; 564/208

[56] References Cited

U.S. PATENT DOCUMENTS

| | | | |
|---|---|---|---|
| 2,794,029 | 5/1957 | Phillips et al. | 260/348 |
| 2,935,516 | 5/1960 | Frostick, Jr. et al. | 260/348.5 |

FOREIGN PATENT DOCUMENTS

| | | |
|---|---|---|
| 0190609 | 8/1986 | European Pat. Off. |
| 0434546 | 6/1991 | European Pat. Off. |
| 1205350 | 4/1958 | France |
| 1206666 | 4/1958 | France |
| 1243106 | 12/1959 | France |
| 1364651 | 3/1963 | France |
| 0215650 | 10/1985 | Japan |
| 62-81378 | 4/1987 | Japan |
| 2185050 | 8/1987 | Japan |
| 2025970 | 1/1980 | United Kingdom |
| 2055821 | 3/1981 | United Kingdom |

OTHER PUBLICATIONS

Chow et al., "Homo-and Copolymers of Vinyl Este s, Acrylates, and Methacrylates of Some Derivatives of Fatty Acids," Journal of Applied Polymer Science, vol. 13, pp. 1545–1553 (1969).

*Primary Examiner*—Paul J. Killos
*Attorney, Agent, or Firm*—Millen, White, Zelano & Branigan

[57] ABSTRACT

An unsaturated (meth)acrylic compound of formula:

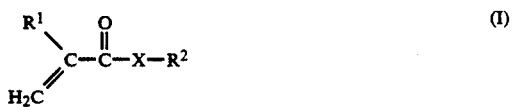

($X=O$, S, NH, $NR^3$ ($R^3=C_{1-12}$-alkyl) or $O-(CH_2)_n$ (where $n=1-16$ approximately); $R^2=C_{2-20}$ straight-chain or branched alkyl, monocyclic or polycyclic cycloalkyl or heterocycloalkyl, or alkylaryl hydrocarbon chain, comprising an olefinic double bond in the chain, or at the end of the chain in the case of alkyl or alkylaryl, or an exocyclic or endocyclic olefinic double bond in the case of monocyclic or polycyclic cycloalkyl or heterocycloalkyl; and $R^1=H$ or $C_{1-5}$-alkyl), is reacted at 10°-60° C. with at least one oxidizing compound (hydrogen peroxide) in the presence of at least one catalyst (alkali metal molybdates and tungstates) and in the presence of at least one phase transfer agent and when $R^2=$polycyclic cycloalkyl or hetercycloalkyl, an organic peracid or hydrogen peroxide in the presence of at least one heteropolyacid. To open the epoxide function, the epoxide obtained is reacted with a compound chosen from strong inorganic acids, boron trifluoride etherate complexes, acid salts in the presence of the corresponding acid, halides of trialkylsilanes or trialkoxysilanes, and ketones in the presence of cationic resins.

13 Claims, No Drawings

SELECTIVE EPOXIDATION OF UNSATURATED (METH)ACRYLATES, NEW FUNCTIONAL (METH)ACRYLATES, AND POLYMERS THEREOF

BACKGROUND OF THE INVENTION

The present invention relates to the selective epoxidation of unsaturated (meth)acrylates allowing the production of new functional (meth)acrylates, and to the use of the latter for the synthesis of new polymers.

The epoxidation of unsaturated organic compounds by means of hydrogen peroxide and a heavy metal acid salt converted in situ into a corresponding peracid salt has been known for some time. Thus, U.S. Pat. Nos. 2,833,787 and 2,833,788 describe the epoxidation of non-conjugated ethylenic compounds, for example monoethylenic alcohols, by means of hydrogen peroxide and sodium pertungstate at a pH of between 3 and 7. Similarly, the article published in J. Org. Chem., Vol. 24, pages 54–55 (January 1959) describes the epoxidation of $\alpha,\beta$-unsaturated acids by means of hydrogen peroxide and sodium tungstate at a pH of between 4 and 5.5.

The epoxidation of olefins by means of hydrogen peroxide and molybdenum compounds is also disclosed in Angew. Chem. Int. Ed. Engl. 21 (1982) 734–750. Similarly, J. Org. Chem. (1983), Vol. 48, 3831–3833 describes the epoxidation of olefins at 70° C. under phase transfer catalysis conditions by means of dilute hydrogen peroxide (at a concentration of less than 10%) and a water-soluble alkali metal tungstate, at pH 1.6 and in the presence of a phase transfer agent such as a quaternary ammonium or phosphonium halide, the molar ratio of hydrogen peroxide to the olefin being 0.6. The article published by J. Org. Chem. (1985) Vol. 50, 2688–2690 describes a similar reaction carried out at 50° C. in the presence of complexes of molybdenum and monodentate ligands, the molar ratio of hydrogen peroxide to the olefin being 0.2.

Finally, it is known to epoxidize olefins at 60° C. in chloroform, in the presence of a catalyst formed from molybdophosphoric or tungstophosphoric acid and cetylpyridinium chloride, by means of concentrated (35%) hydrogen peroxide and the molar ratio of hydrogen peroxide to the olefin being 1.5 or 1: on this subject reference may be made to J. Org. Chem. (1987), Vol. 52, 1868–1870 and J. Org. Chem. (1988), Vol. 53, 3587–3593.

Moreover, the U.S. Pat. No. 3,459,775 describes the epoxidation of vinylnorbornene (meth)acrylate at a temperature of 50° C., for a period of 7 to 9 hours, by means of peracetic acid. 2-Epoxyethylbicyclo[2.2.1-]hept-5(6)-yl (meth)acrylate is obtained under these conditions in a yield not exceeding 42%. Similarly, the patent application JP-A-62/81 378 describes the epoxidation of dicyclopentenyloxyethyl acrylate at a temperature of 60° C., for 2 hours, by means of hydrogen peroxide at a concentration of 35%. The epoxidized acrylate is obtained under these conditions in a yield not exceeding 48%.

SUMMARY OF THE INVENTION

The problem which the present invention proposes to resolve, taking account of the teaching of the prior art recalled above relating to the epoxidation of organic compounds having ethylenic unsaturation, such as olefins, alcohols, acids or some (meth)acrylates, involves developing the conditions for the selective epoxidation of non-acrylic unsaturations in unsaturated (meth)acrylic compounds in particular by means of hydrogen peroxide. During the work which led to the present invention, the epoxidation of some unsaturated (meth)acrylates by means of organic peracids was also carried out successfully. However, this latter method proved to have a less general scope than that using hydrogen peroxide and, on the other hand, it requires the removal at the end of the operation of the organic acid formed by the reaction.

Thus, a first subject of the present invention comprises a process for the epoxidation of an unsaturated (meth)acrylic compound of general formula:

in which:
X is chosen from oxygen and sulphur atoms, the NH radical, the radicals $NR^3$ in which $R^3$ is an alkyl group having from 1 to 12 carbon atoms, and the oxyalkylene radicals $O-(CH_2)_n$ in which n is an integer ranging from 1 to 16 approximately, $R^2$ denotes a hydrocarbon chain comprising from 2 to 20 carbon atoms, chosen from straight-chain or branched alkyl, monocyclic or polycyclic cycloalkyl or heterocycloalkyl, and alkylaryl chains, the said hydrocarbon chain comprising an olefinic double bond in the chain, or at the end of the chain in the case of an alkyl or alkylaryl chain, or an exocyclic or endocyclic olefinic double bond in the case of a monocyclic or polycyclic cycloalkyl or heterocyclo-alkyl chain, and $R^1$ is chosen from a hydrogen atom and alkyl radicals having from 1 to 5 carbon atoms, by the action, on the said unsaturated (meth)acrylate, at a temperature of between 10° C. and 60° C. approximately, of at least one oxidising compound chosen from:
hydrogen peroxide in the presence of at least one catalyst chosen from alkali metal molybdates and tungstates and in the presence of at least one phase transfer agent, and
when $R^2$ denotes a polycyclic cycloalkyl or heterocycloalkyl chain, an organic peracid or hydrogen peroxide in the presence of at least one heteropolyacid.

A very large number of unsaturated (meth)acrylic compounds may be epoxidised in accordance with the process according to the invention. The following may be mentioned in particular: alkyl acrylates and methacrylates, dicyclopentenyloxyethyl acrylate and methacrylate, cinnamyl acrylate and methacrylate, vinylnorbornyl acrylate and methacrylate, crotyl acrylate and methacrylate, decenyl acrylate and methacrylate, dicyclopentenyl acrylate and methacrylate, ethylidenenorbornyl acrylate and methacrylate, etc.

Preferably, the unsaturated (meth)acrylate of formula (I) is stabilised, before reaction, by the addition of an effective amount of at least one compound such as hydroquinone, hydroquinone monomethyl ether, phenothiazine, N,N-diethylhydroxylamine, nitrobenzene, di-tert-butylcatechol, p-anilinophenol, di-(2-ethylhexyl)octylphenyl phosphite, methylene blue and their mixtures in any proportions. An effective amount is understood to be a proportion of generally between 0.05 and 0.5% approximately by weight of the unsaturated methacrylate of formula (I).

The reaction on which the process according to the invention is based must be carried out at a moderate temperature avoiding temperatures higher than about 50° C., which are often the cause of the polymerization of the unsaturated (meth)acrylic compound or of its epoxide, and temperatures lower than about 10° C., for reasons of kinetics. The reaction according to the invention is preferably carried out in the presence of an organic solvent, or a mixture of organic solvents, which may be chosen, in particular, from chlorinated solvents, such as 1,2-dichloroethane, chloroform, carbon tetrachloride, trichloromethane or dichloromethane, and aromatic solvents such as benzene and toluene, and in an amount such that the ratio by volume of compound to be epoxidized/solvent is higher than about 1.5.

When the reaction according to the invention is carried out in the presence of at least one phase transfer agent, the latter is chosen, in particular, from the family of, for example, quaternary ammonium halide salts, such as tricaprylylmethylammonium chloride, tetrabutylammonium chlorides, tetrabutylammonium bromide and tetrabutylammonium iodide, or, for example, from the family of quaternary phosphonium halide salts, such as tetrabutylphosphonium chloride, tetrabutylphosphonium bromide and tributylhexadecylphosphonium bromide, or may also be tetrabutylammonium hydrogen sulphate. The phase transfer agent is preferably used in a molar proportion, relative to the compound to be epoxidized, of at least 0.5% and more particularly of between 1% and 3%.

In the process according to the invention, the molar ratio between hydrogen peroxide and the unsaturated (meth)acrylic compound is very important: it is at least one mole, preferably 1.5 to 3 moles, of hydrogen peroxide per mole of unsaturated (meth)acrylic compound. Similarly, the concentration of the hydrogen peroxide, used in aqueous solution, is not without influence on the yield and on the selectivity of the epoxidation reaction: it is preferably between 5% and 50% approximately and more particularly between 10% and 35%. Another important reaction condition is the pH of the mixture: it will preferably be chosen between 1.0 and 3.5 approximately and more particularly between 1.5 and 2.5, and will be adjusted by means of the necessary amount of an acid such as phosphoric acid and/or sulfuric acid.

When the epoxidation reaction is carried out in the presence of an alkali metal molybdate or tungstate, the latter may be represented by the formula $M_2M'O_4$ in which M is preferably chosen from lithium, sodium and potassium and M' is chosen from molybdenum and tungsten. This catalyst is preferably used in a molar proportion, relative to the compound to be epoxidised, of at least 0.1% and more particularly of between 0.5% and 5%. A catalyst of this type may also be modified by the addition of an inorganic acid, such as phosphoric acid.

When an organic peracid is chosen as the oxidising compound for the epoxidation reaction, the said organic peracid is preferably a peracid comprising from 1 to 4 carbon atoms, such as performic acid or peracetic acid. It may be formed in situ by the action of hydrogen peroxide on the corresponding organic acid (formic or acetic acid), for example in the presence of a little sulfuric acid as catalyst. In the case where an organic peracid is used as oxidizing agent, the use of a metal catalyst and/or of a phase transfer agent is no longer necessary.

When the combination of hydrogen peroxide and a heteropolyacid is chosen as oxidising agent for the epoxidation reaction, the said heteropolyacid has the general formula:

$$H_nA_aD_cO_y \cdot xH_2O$$

in which:

A represents phosphorus, boron, silicon, germanium, tin, arsenic, antimony, copper, nickel, cobalt, iron, cerium, thorium, chromium or a mixture of at least two of these elements;

D represents molybdenum, tungsten, vanadium or a combination of at least two of these elements;

a is a number from 0.1 to 10;

c is a number from 6 to 18;

n is the number of acid hydrogens in the heteropolyacid and is a number higher than 1;

y is the number of oxygens in the heteropolyacid and is a number of the order of 10 to 70; and x is the number of moles of water of crystallization and is a number of from 0 to about 40.

These heteropolyacids are known and they may be prepared by known techniques. Heteropolyacids of particular interest are phosphomolybdic acid ($H_3PMo_{12}O_{40}$), phosphotungstic acid ($H_3PW_{12}O_{40}$) and silicotungstic acid ($H_4SiW_{12}O_{40}$).

The reaction according to the invention leads, with a degree of conversion which is most often higher than 70%, selectively to the epoxidation of the olefinic double bond in the chain $R^2$ so as to form a (meth)acrylic epoxide, which could be represented by the formula:

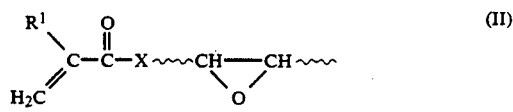   (II)

in which $R^1$ and X have the abovementioned meaning. The latter compound is preferentially converted to the epoxide of formula:

   (III)

resulting from the epoxidation of the acrylic double bond, which nevertheless is able to form significantly under particular conditions, and also, more rarely, the diepoxide of formula:

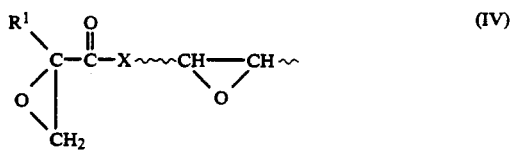   (IV)

resulting from the simultaneous epoxidation of the two olefinic and acrylic double bonds. This result of the invention is particularly surprising insofar as, to date, according to the prior documents already cited, the epoxidation of unsaturated (meth)acrylates proceeded with low yields despite reaction temperatures higher than those specified by the present invention.

A second subject of the present invention comprises a new family of (meth)acrylic epoxides, capable of being prepared by the process described above and corresponding to the general formula:

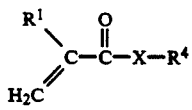
(V)

in which:

- X is chosen from oxygen and sulphur atoms, the NH radical, the radicals $NR^3$ in which $R^3$ is an alkyl group having from 1 to 12 carbon atoms, and the oxyalkylene radicals $O—(CH_2)_n$ in which n is an integer ranging from 3 to 16 approximately,
- $R^1$ is chosen from a hydrogen atom and alkyl radicals having from 1 to 5 carbon atoms, and
- $R^4$ denotes a hydrocarbon chain comprising from 2 to 20 carbon atoms, chosen from straight-chain or branched alkyl, monocyclic or polycyclic cycloalkyl or heterocycloalkyl, and alkylaryl chains, the said hydrocarbon chain comprising an oxirane group in the chain, or at the end of the chain in the case of an alkyl or alkylaryl chain, or an exocyclic or endocyclic oxirane group in the case of a monocyclic or polycyclic cycloalkyl or heterocycloalkyl chain, with the exception of vinylnorbornyl and dicyclopentenyloxyethyl epoxides.

Amongst the latter compounds, those which may be mentioned in particular are epoxidized methacrylates of formula:

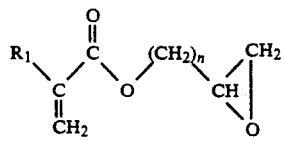
(VI)

in which $R_1$ is chosen from a hydrogen atom and a methyl radical and n is an integer ranging from 3 to 16, (meth)acrylates of formula:

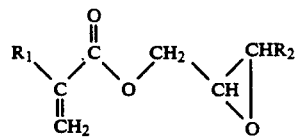
(VII)

in which $R_1$ is chosen from a hydrogen atom and a methyl radical and $R_2$ is chosen from alkyl radicals having from 1 to 12 carbon atoms and aryl radicals having from 6 to 12 carbon atoms, and also epoxidized (meth)acrylates of formulae:

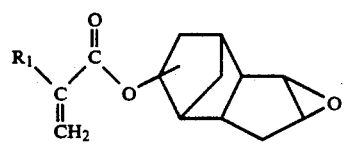
(VIII)

and

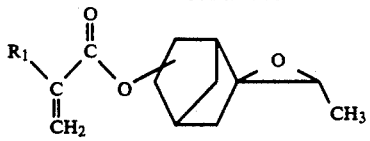
(IX)

in which $R_1$ is chosen from a hydrogen atom and a methyl radical.

The following may be mentioned as representative examples of this family: 4,5-epoxypentyl acrylate and methacrylate, 5,6-epoxyhexyl acrylate and methacrylate, 6,7-epoxyheptyl acrylate and methacrylate, 7,8-epoxyoctyl acrylate and methacrylate, 8,9-epoxynonyl acrylate and methacrylate, 9,10-epoxydecyl acrylate and methacrylate and 11,12-epoxydodecyl acrylate and methacrylate. Examples of new bifunctional (meth)acrylates of formula (II) are 2,3-epoxybutyl acrylate and methacrylate and 3-phenyl-2,3-epoxypropyl acrylate and methacrylate. Finally, the new epoxidized (meth)acrylates of formulae (VIII) and (IX) are, respectively, octahydro-2,5-methano-2H-undeno[1,2-b]oxyrenyl acrylate and methacrylate and 5(6)-hydroxy-2-[2,1'-epoxyethyl]bicyclo[2.2.1]heptane acrylate and methacrylate.

Another subject of the present invention comprises new families, capable of being formed in subsidiary amounts by the process described above, of epoxides of formula (III) and diepoxides of formula:

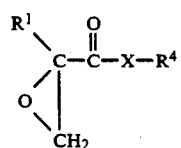
(X)

in which $R^1$, X and $R^4$ have the same meanings as in formula (V). These subsidiary products of the epoxidation reaction according to the invention may, in fact, be extracted and isolated from the reaction mixture by the customary separation techniques.

Yet a further subject of the present invention comprises a process for opening the epoxide function of a (meth)acrylic epoxide of formula (V), characterised in that the said (meth)acrylic epoxide is reacted with a compound chosen from strong inorganic acids, boron trifluoride etherate complexes, acid salts in the presence of the corresponding acid, such as sodium acetate or sodium propionate in the presence of acetic acid or propionic acid respectively, the halides of trialkylsilanes or trialkoxysilanes and in particular of trimethylsilane, triethylsilane, trimethoxysilane or triethoxysilane, more particularly trimethylchlorosilane, and ketones in the presence of cationic resins. Depending on the nature of the reactive compound chosen, the reaction conditions may vary somewhat and the nature of the product resulting from the opening of the epoxide function also varies.

Thus, when the reactive compound is a strong inorganic acid such as concentrated sulfuric acid or concentrated hydrochloric acid, the latter is generally used in less than the stoichiometric amount relative to the epoxide and the reaction generally takes place in the presence of water at a temperature of between +10° C. and +50° C. ap-proximately and for a period which can be up to about 50 hours. The opening product formed is then identified as the diol corresponding to the (meth)a- crylic epoxide of formula (V) and may be represented schematically by the formula:

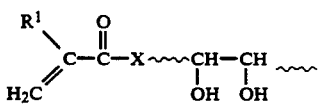

When the reactive compound is a boron trifluoride etherate complex, the latter is used in an essentially stoichiometric amount relative to the epoxide and the reaction generally takes place in the presence of a saturated alcohol having from 1 to 4 carbon atoms as reactive solvent and at a temperature of between −50° C. and +30° C. approximately and for a period which can be up to 30 hours approximately. The opening product formed is then identified as an ether-alcohol which may be represented schematically by the formula:

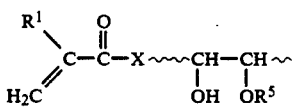

in which $R^5$ is an alkyl radical having from 1 to 4 carbon atoms originating from the solvent alcohol.

When the reactive compound is an acid salt, the latter is used in excess in a ratio of 2 to 10 moles approximately per mole of epoxide. The reaction is performed using the corresponding acid as solvent at a temperature of between 20° and 60° C. approximately and for a period which can be up to about 72 hours. The opening product formed is then identified as an acetate-alcohol which may be represented schematically by the formula:

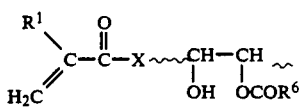

in which $R^6$ is an alkyl or aryl group originating from the corresponding acid salt.

A reactive compound which may be mentioned by way of example is sodium acetate, in the presence of acetic acid, $R^6$ then representing $CH_3$.

When the reactive compound is a trialkylsilane halide or trialkoxysilane halide, the latter is used in a substantially stoichiometric amount; 1 mole to 1.33 moles approximately per 1 mole of epoxide. The reaction is generally carried out in the presence of a catalyst such as a phosphine, for example triphenylphosphine, or a quaternary ammonium halide, for example tributylammonium bromide, used in a catalytic amount, 0.1 to 1 mol-% approximately relative to the epoxide, and in the presence of a solvent or of a mixture of solvents, for example chloroform, carbon tetrachloride, methylene chloride or 1,2-dichloroethane. The amount of solvent used is approximately 5 to 10 times by weight that of the epoxide. The reaction generally takes place at a temperature of between 0° and 25° C. and for a period of between 10 minutes and 1 hour. The opening product formed is then a mixture of silylated chloro-ether which may be represented schematically by the formula:

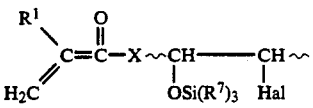

in which:
Hal is a halide and
$R^7$ is an alkyl or alkoxy group originating from the trialkylsilane halide or trialkoxysilane halide employed.

It should be noted that this compound leads, via hydrolysis in water or by means of ambient moisture, to the formation of the corresponding chloro-alcohol represented schematically by the formula:

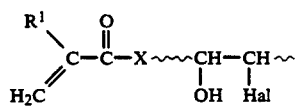

When the reactive compound is a ketone, the reaction generally takes place in the presence of at least one cationic resin used in an amount of 20 to 50% approximately by weight relative to the (meth)acrylic epoxide, at a temperature of between 10° C. and 50° C. approximately and for a period of between 30 minutes and 3 hours approximately. Ketones which may be used are, in particular, acetone, methyl ethyl ketone, acetophenone, pentan-3-one or methyl isobutyl ketone, in a ratio of from 1 to 2.5 moles approximately per 1 mole of (meth)acrylic epoxide. Cationic resins which may be used are any acid ion exchange resin, such as, for example, a sulphonated resin of small particle size. The opening product formed is then a dioxolane which may be presented schematically by the formula:

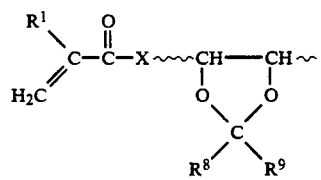

in which $R^8$ and $R^9$ are alkyl or aryl groups originating from the ketone.

Preferably, the epoxidized methacrylates of formula (II) are stabilized, before reaction, by the addition of an effective amount of at least one compound such as hydroquinone, hydroquinone monomethyl ether, phenothiazine, N,N-diethylhydroxylamine, nitrobenzene, di-tert-butylcatechol, p-anilinophenol, di-(2-ethylhexyl)octylphenyl phosphite, methylene blue and their mixtures in any proportions. An effective amount is understood to be a proportion of generally between 0.05 and 1% approximately by weight of the epoxidised methacrylate of formula (II).

The reactions involving opening of the epoxide function which have just been described are applicable to all of the methacrylic epoxides of formula (V) but also to glycidyl, 2-epoxyethylbicyclo[2.2.1]hept-5(6)-yl and epoxydicyclopentenyloxyethyl (meth)acrylates.

The new epoxidised (meth)acrylates according to invention, and also the diols, ether-alcohols and dioxolanes which derive therefrom by opening of the epoxide function as described above, are compounds having a weak odor. They polymerise easily and also copolymerise with monomers containing an ethylenic unsaturation, such as ethylene, and also:

- an alkyl acrylate or methacrylate in which the straight-chain or branched alkyl group, which if necessary is substituted, for example by at least one halogen atom such as chlorine or fluorine and/or by at least one hydroxyl group, has from 1 to 20 carbon atoms,
- an aryl acrylate or methacrylate, such as benzyl methacrylate,
- a vinyl-aromatic hydrocarbon, such as styrene, vinyltoluene, alpha-methylstyrene, 4-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene,
- an unsaturated nitrile, such as acrylonitrile or methacrylonitrile,
- an N-substituted maleimide, such as N-ethylmaleimide, N-isopropylmaleimide, N-n-butylmaleimide, N-iso-butylmaleimide, N-tert-butylmaleimide, N-n-octyl-maleimide, N-cyclohexylmaleimide, N-benzylmaleimide and N-phenylmaleimide,
- an unsaturated dicarboxylic acid anhydride, such as maleic anhydride, itaconic anhydride, citraconic anhydride or tetrahydrophthalic anhydride, acrylic or methacrylic acid,
- a polyol acrylate or methacrylate, such as the diacrylates and dimethacrylates of ethylene glycol, propylene glycol, butane-1,3-diol, butane-1,4-diol, hexane-1,6-diol, neopentyl glycol, cyclohexane-1,4-diol, cyclohexane-1,4-dimethanol, 2,2,4-trimethylpentane-1,3-diol, 2-ethyl-2-methylpropane-1,3-diol, 2,2-diethylpropane-1,3-diol, diethylene glycol, dipropylene glycol, triethylene glycol, tripropylene glycol, tetraethylene glycol, tetrapropylene glycol, trimethylolethane, trimethylolpropane, glycerol and pentaerythritol, the triacrylates and trimethacrylates of trimethylolethane, trimethylolpropane, glycerol and pentaerythritol, the tetraacrylates and tetramethacrylates of pentaerythritol, the di(meth)acrylates to hexa(meth)acrylates of dipentaerythritol and the poly(meth)acrylates of monoethoxylated or polyethoxylated or monopropoxylated or polypropoxylated polyols, such as triethoxylated trimethylolpropane triacrylate and trimethacrylate and tripropoxylated trimethylolpropane triacrylate and trimethacrylate; tripropoxylated glycerol triacrylate and trimethacrylate; and tetraethoxylated pentaerythritol triacrylate, trimethacrylate, tetraacrylate and tetramethacrylate,
- an acrylamide or methacrylamide, dialkyaminoalkyl acrylate or methacrylate and their quaternary salts, 2-(2-norbornyloxy)ethyl acrylate and methacrylate and 2-(2-dimethanodecahydronaphthyloxy)ethyl acrylate and methacrylate, and
- acrylic and methacrylic oxazolidones chosen from those of formula:

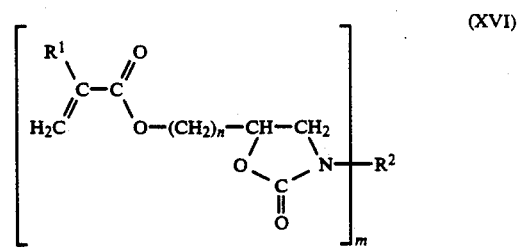

and those of formula:

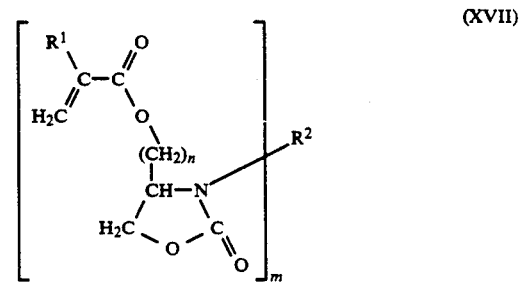

in which formulae:
$R^1$ is chosen from a hydrogen atom and a methyl radical,
n is an integer ranging from 1 to 12,
m is an integer ranging from 1 to 3, and
$R^2$ is a straight-chain, branched or cyclic alkyl, or an aromatic, hydrocarbon radical having from 5 to 12 carbon atoms,
it being possible for the said oxazolidones to be obtained by reaction, at between 30° C. and 90° C., of a compound carrying a (meth)acrylic function with a compound carrying at least one isocyanate function,
acrylic and methacrylic compounds chosen from those of formula:

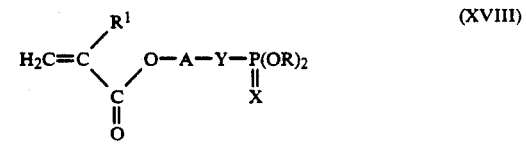

in which:
$R^1$ is chosen from a hydrogen atom and a methyl radical,
A is chosen from the radicals $(CH_2)_n$ for which n is an integer from 2 to 12 and the radical $—(CH_2CH_2O)_d—CH_2CH_2—$, d being an integer ranging from 1 to 20,
X is chosen from sulphur and oxygen atoms,
Y is chosen from sulphur and oxygen atoms, on condition that X is a sulphur atom and Y is an oxygen atom when A is the radical $—(CH_2CH_2O)_d—CH_2CH_2—$ and
R is chosen from alkyl radicals having from 1 to 20 carbon atoms and the $—(CH_2)_pSR^3$ groups in which p is an integer ranging from 3 to 12 and $R^3$ is an
alkyl radical having from 1 to 20 carbon atoms, those of formula:

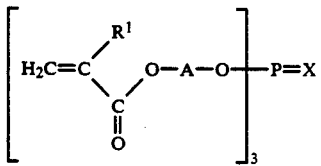

(XIX)

in which:
R$^1$ is chosen from a hydrogen atom and a methyl radical,
A is chosen from the radicals (CH$_2$)$_n$ for which n is an integer from 2 to 12 and the radical —(CH$_2$CH$_2$O)$_d$—CH$_2$CH$_2$—, d being an integer ranging from 1 to 20, and
X is chosen from sulfur and oxygen atoms,
and those of formula:

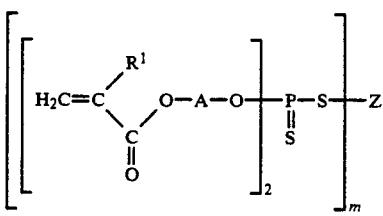

(XX)

in which:
R$^1$ is chosen from a hydrogen atom and a methyl radical,
A is chosen from the radicals (CH$_2$)$_n$ for which n is an integer from 2 to 12,
m is an integer ranging from 1 to 3, and
Z is chosen from a hydrogen atom, the radicals R$^2$QH, R$^2$ being an alkyl radical having from 2 to 12 carbon atoms and Q being chosen from oxygen and sulphur atoms, and the atoms of metals of groups IA, IIA, IIIA, IB, IIB, VIB, VIIB and VIII of the Periodic Classification, on condition that Z is chosen from a hydrogen atom and the radicals R$^2$OH when m=1 and that m is the valency of Z when Z is a metal.

Compounds of this type may be prepared by reaction of an acrylic or methacrylic compound of formula:

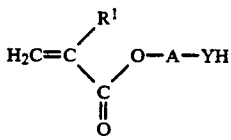

(XXI)

in which R$^1$, A and Y have the same meanings as in formula (X), with a pentavalent phosphorus compound, it being possible for the latter to be, for example, a compound of formula PXT$_3$ in which X has the same meaning as in the formula (X) and T denotes a halogen atom, or a phosphorus compound of formula:

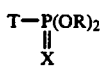

(XXII)

in which R and X have the same meanings as in formula (I) and T denotes a halogen atom, or the pentasulfide P$_2$S$_5$, acrylic and methacrylic compounds chosen from those of formula:

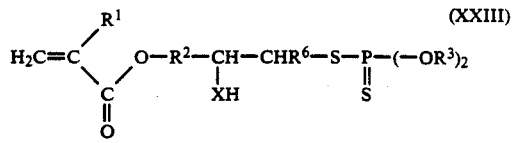

(XXIII)

and those of formula:

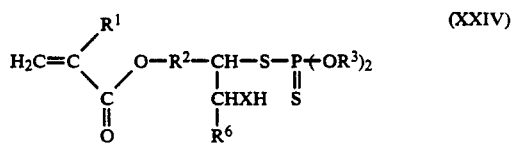

(XXIV)

in which formulae:
R$^1$ is chosen from a hydrogen atom and a methyl radical,
X is a heteroatom chosen from oxygen and sulphur,
R$^2$ is chosen from straight-chain or branched alkylene, monocyclic or polycyclic cycloalkylene and heterocycloalkylene, and alkylarylene and arylalkylene groups comprising from 1 to 12 carbon atoms,
R$^6$ is chosen from a hydrogen atom and alkyl and aryl radicals having from 1 to 12 carbon atoms, and
R$^3$ is chosen from alkyl and aryl radicals having from 1 to 20 carbon atoms, the groups —(CH$_2$)$_p$SR$^4$ in which p is an integer ranging from 2 to 12 and R$^4$ is an alkyl radical having from 1 to 20 carbon atoms or a monocyclic or polycyclic cycloalkyl group having from 4 to 10 carbon atoms, each ring in the said group comprising from 4 to 6 members, and the groups

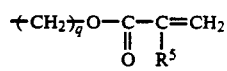

in which q is an integer ranging from 2 to 12 and R$^5$ is chosen from a hydrogen atom and a methyl radical. Compounds of this type may be prepared by reaction of an acrylic or methacrylic epoxide or episulfide of formula:

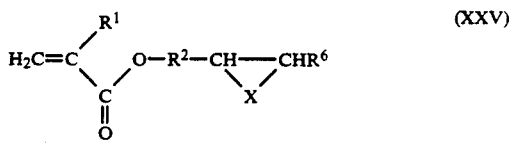

(XXV)

in which R$^1$, R$^2$, R$^6$ and X have the same meanings as in formula (XI), with a thiophosphorus compound of formula:

(XXVI)

Polymers and copolymers of this type, are obtained by (co)polymerizing at least one sulfur-containing acrylic compound according to the invention and, if necessary, at least one copolymerisable comonomer, as defined above, in the presence of at least one free radical initiator such as a peroxide, a hydrogen peroxide or a diazo compound. The (co)polymerization is generally carried out at a temperature of between 50° C. and 120° C. approximately and using one of the monomers as solvent. It may also take place in emulsion in water, at a temperature of between about 50° C. and 100° C., in the presence of at least one surface-active agent.

When the comonomer is ethylene, a temperature of 140° to 300° C. approximately and a pressure of 1000 to 3000 bars approximately may be used. When the comonomer is a vinyl-aromatic hydrocarbon, a temperature of 80° to 200° C. approximately may be used.

The new (meth)acrylic epoxides according to the invention and also the products resulting from opening of the epoxide function, such as the corresponding diols of formula (VII), the corresponding ether-alcohols of formula (VIII) and the corresponding dioxolanes of formula (IX), because of their weak odor and their low viscosity, may find applications as modifying agents in the inks, adhesives, paints, coatings and resins sectors.

The following examples are given by way of illustration and do not limit the present invention.

EXAMPLE 1

A solution consisting of 3 millimoles of sodium tungstate $Na_2WO_4.2H_2O$, 5.1 millimoles of 34% phosphoric acid and 120 millimoles of 20% aqueous hydrogen peroxide, the pH of which has been adjusted to 1.9 using a 30% sulfuric acid solution, is added dropwise, in the course of 15 minutes, to a solution consisting of 0.6 millimole of tricaprylylmethylammonium chloride (marketed under the name ALIQUAT 336 by Aldrich) and 60 millimoles of allyl methacrylate (marketed by the Applicant) in 15 ml of methylene chloride. The mixture is stirred vigorously at 20° C. A few minutes after the addition, a yellow coloration appears and then fades. The reaction is monitored by gas phase chromatography by analysis of regular samples. After 96 hours an acid solution of iron sulphate is added to the reaction mixture in order to destroy the peroxides present in the mixture. At this stage the degree of conversion of the reaction C (expressed in %) and the selectivities S for epoxide of formula (II) (in this case glycidyl methacrylate) and for epoxide of formula (III) indicated in Table 1 below are calculated.

EXAMPLE 2

A mixture of 0.24 millimole of tungstophosphoric acid $H_3PW_{12}O_{40}$ and 120 millimoles of 35% aqueous hydrogen peroxide is added dropwise in the course of 15 minutes to a solution of 60 millimoles of dicyclopentenyloxyethyl methacrylate in 15 ml of chloroform. The mixture is stirred vigorously at 45° C. After 3 hours the reaction is stopped in the same way as in Example 1. The conversion and the selectivities are indicated in Table I below.

EXAMPLE 3

A solution consisting of 1 millimole of sodium tungstate $Na_2WO_4.2H_2O$, 1.7 millimoles of 34% phosphoric acid and 40 millimoles of 20% aqueous hydrogen peroxide, the pH of which is adjusted to 1.7 using a 30% sulfuric acid solution, is added dropwise in the course of 5 minutes to a mixture of 0.4 millimole of tricaprylylmethylammonium chloride and 20 millimoles of dicyclopentenyloxyethyl methacrylate. The mixture is stirred vigorously at 40° C. After 2.5 hours the reaction is stopped in the same way as in Example 1. The conversion and the selectivities are indicated in Table I below.

EXAMPLES 4 TO 7

The operating method of Example 3 is repeated dissolving the mixture of tricaprylylmethylammonium chloride and methacrylate in 15 ml of a solvent. The latter is, respectively, chloroform (Example 4), carbon tetrachloride (Example 5), 1,2-dichloroethane (Example 6) and toluene (Example 7). After a reaction time of 5 hours (Examples 5 and 7) or 6 hours (Examples 4 and 6), the conversion and the selectivities are those indicated in Table I below.

TABLE I

| Example | C | S(II) | S(III) |
|---------|-----|-------|--------|
| 1 | 74 | 94 | 6 |
| 2 | 100 | 100 | 0 |
| 3 | 98 | 100 | 0 |
| 4 | 98 | 100 | 0 |
| 5 | 92 | 100 | 0 |
| 6 | 99 | 100 | 0 |
| 7 | 96 | 100 | 0 |

EXAMPLES 8 TO 10 x grams of epoxidised (meth)acrylate and y grams of methyl methacrylate and then 0.2 gram of azobisisobutyronitrile are introduced into a reactor. After having purged with nitrogen, the reactor is plunged into a bath at 83° C. The temperature (expressed in degrees Celsius) $T_{exo}$ of the exothermic peak is recorded and, after the temperature has returned to that of the thermostatic bath (83° C.), isothermal boiling is carried out for 5 hours. On leaving the reactor, the polymer obtained is washed with methanol, ground and then dried under a vacuum of 10 mmHg at 40° C. Table II below indicates, in addition to the yield (yld) of polymer expressed as a percentage, the glass transition temperature Tg of the polymer (expressed in degrees Celsius) and also the solubility of the polymer in various solvents, expressed either as a percentage by weight or by a visual observation (swelling for example).

The epoxide used in the following examples is either dicyclopentenyloxyethyl methacrylate (Example 8) or dicyclopentenyloxyethyl acrylate (Examples 9 and 10).

TABLE II

| Example | 8 | 9 | 10 | 11 |
|---------|-----|-----|-----|-----|
| x | 10 | 10 | 6 | 5 |
| y | 0 | 0 | 4 | 5 |
| $T_{exo}$ | 133 | 118 | nd | — |
| yld | 90 | 80 | 85 | 85 |
| Tg | +45 | +39 | +60 | +75 |
| acetone | swells | 0 | 50 | 50 |
| methanol | swells | nd | nd | nd |
| heptane | 0 | 0 | 0 | 0 |
| ethyl acetate | 60 | 50 | 50 | 50 | nd: not determined

EXAMPLE 11

5 grams of methyl methacrylate, 5 grams of dicyclopentenyloxyethyl methacrylate, 10 grams of methyl ethyl ketone and 0.2 gram of azobisisobutyronitrile are introduced into a reactor. After having purged with a stream of nitrogen, the reactor is plunged into a thermostatic bath at 83° C. and exothermal boiling is carried out for 5 hours. At the end of the reaction, the polymer is treated and characterized as in Examples 8 to 10 (see Table II).

EXAMPLE 12

The epoxide (III) of formula

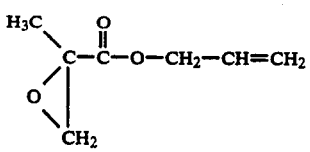

formed as subsidiary product during the synthesis of Example 1 was isolated from the reaction mixture by extraction of the aqueous phase with dichloromethane, washing of the organic phase with water, drying over magnesium sulphate and then evaporation of the solvents. It was then purified by chromatography on silica gel, the eluent being a mixture of ethyl acetate (15%), and petroleum ether (85%), and then characterized by:

Infrared; spectrophotometry using a PERKIN ELMER 841 spectrometer: the spectrum obtained (FIG. 1) comprises characteristic bands at 1745 cm$^{-1}$, 1650 cm$^{-1}$, 1175 cm$^{-}$, 1145 cm$^{-1}$ and 1080 cm$^{-1}$.

Proton nuclear magnetic resonance, using a JEOL PMX 60SI spectrometer: the spectrum obtained (FIG. 2) shows chemical shifts at 5.7–6.1 ppm (m, 1H), 5.1–5.4 ppm (m, 2H), 4.5–4.7 ppm (m, 2H), 3.05 ppm (d, 1H), 2.7 ppm (d, 1H) and 1.5 ppm (s, 3H).

EXAMPLE 13

During the isolation and the purification of the glycidyl methacrylate obtained in the course of the synthesis of Example 1, the presence of a small proportion of diepoxide (IV) of formula

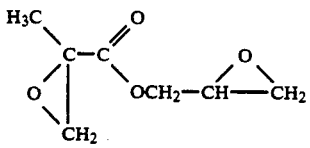

is detected and this product was purified and then characterised as in Example 12 by:

Infrared spectrophotometry: the spectrum obtained (FIG. 3) comprises characteristic bands at 2999 cm$^{-1}$, 1740 cm$^{-1}$1, 1174 cm$^{-1}$, 1145 cm$^{-1}$, 1078 cm$^{-1}$, 1014 cm$^{-1}$, 908 cm$^{-1}$ and 864 cm$^{-1}$.

Proton nuclear magnetic resonance: the spectrum obtained shows chemical shifts at 3.7–4.5 ppm (m, 2H), 2.5–3.3 ppm (m, 5H) and 1.5 ppm (s, 3H).

EXAMPLE 14

The dicyclopentenyloxyethyl methacrylate epoxide prepared in Example 2 was characterised as in Example 12 by:

Infrared spectrophotometry: the spectrum obtained (FIG. 4) comprises characteristic bands at 2954 cm$^{-1}$, 1722 cm$^{-1}$, 1639 cm$^{-1}$, 1453 cm$^{-1}$, 1169 cm$^{-1}$, 1107 cm$^{-1}$, 941 cm$^{-1}$ and 836 cm$^{-1}$.

Carbon 13 nuclear magnetic resonance: chemical shifts at 167.1 ppm, 136.2 ppm, 125.7 ppm, 77.2–81.8 ppm, 65.9 ppm, 59.6–62.0 ppm, 26.0–52.0 ppm and 18.3 ppm.

Proton nuclear magnetic resonance: the spectrum obtained (FIG. 5) shows chemical shifts at 6.1 ppm (m, 1H), 5.6 ppm (m, 1H), 4.25 ppm (m, 2H), 3.2–3.7 ppm (m, 5H) and 1.2–2.5 ppm (m, 13H).

EXAMPLE 15

10 millimoles of epoxydicyclopentenyloxyethyl methacrylate, 5 millimoles of sulfuric acid in 50 ml of water and 20 ml of tetrahydrofuran are placed in a reactor. The mixture is stirred at 40° C. for 48 hours. The reaction mixture is extracted with methylene chloride and the organic phase is dried over magnesium sulfate and the solvent is then evaporated and the organic reaction products are subjected to chromatography on a silica column, using eluents of increasing polarity: mixture of 85% of petroleum ether and 15% of ethyl acetate, then ethyl acetate and finally methanol. The reaction leads to the formation of the diol of formula

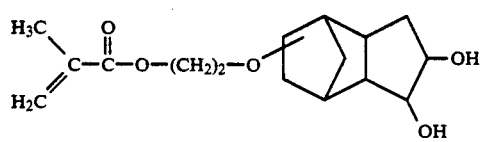

in a yield of 92%.

This product was characterized by:

Infrared spectrophotometry: the spectrum obtained (FIG. 6) shows characteristic bands at 3435 cm$^{-1}$, 2955 cm$^{-1}$, 1722 cm$^{-1}$, 1638 cm$^{-1}$, 1452 cm$^{-1}$, 1320 cm$^{-1}$, 1297 cm$^{-1}$, 1166 cm$^{-1}$ and 1106 cm$^{-1}$.

Proton nuclear magnetic resonance: chemical shifts at 6.1 ppm (m, 1H), 5.55 ppm (m, 1H), 3.5–4.4 ppm (m, 7H), 3.3 ppm (m, 2H, OH), and 1.1–2.7 ppm (m, 13H).

Carbon 13 nuclear magnetic resonance: chemical shifts at 166.9 ppm (C=O), 135.2 ppm (>C=), 125.4 ppm (CH$_2$=), 82.1 to 79.3 ppm (CH—O), 65.8–63.6 ppm (CH$_2$—O), 45.1 to 13.8 ppm (CH and CH$_2$) and 17.0 ppm (CH$_3$).

EXAMPLE 16

The operating method of Example 15 is repeated replacing epoxydicyclopentenyloxyethyl methacrylate by glycidyl methacrylate. The reaction mixture is stirred for 2 hours at ambient temperature. The diol of formula

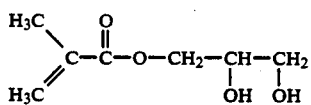

is recovered in a yield of 72%.

This product is characterized by:

Infrared spectroscopy: the spectrum obtained shows characteristic bands at 3399 cm$^{-1}$, 2930 cm$^{-1}$, 1717 cm$^{-1}$, 1638 cm$^{-1}$, 1453 cm$^{-1}$, 1380 cm$^{-1}$, 1323 cm$^{-1}$, 1173 cm$^{-1}$, 1053 cm$^{-1}$, 944 cm$^{-1}$ and 814 cm$^{-1}$.

Proton magnetic resonance: chemical shifts at 6.1 ppm (m, 1H), 5.55 ppm (m, 1H), 4.26 ppm (m, 2H, OH), 4.25–3.40 ppm (m, 5H) and 1.9 ppm (m, 3H).

Carbon 13 magnetic resonance: chemical shifts at 167.2 ppm (C=O), 135.4 ppm (>C=), 125.8 ppm (CH$_2$=), 69.6 ppm (CH—OH), 64.9 ppm (CH$_2$—O), 62.9 ppm (CH$_2$OH) and 17.7 ppm (CH$_3$).

EXAMPLE 17

The operating method of Example 15 is repeated replacing epoxydicyclopentenyloxyethyl methacrylate by 2,3-epoxybutyl methacrylate. The reaction mixture is stirred for 3 hours at ambient temperature. The diol of formula:

$$\underset{H_2C}{\overset{H_3C}{\diagdown}}C=C-\overset{O}{\overset{\|}{C}}-O-CH_2-\underset{OH}{\overset{|}{CH}}-\underset{OH}{\overset{|}{CH}}-CH_3$$

is recovered in a yield of 85%.

This product is characterized by:

Infrared spectroscopy: the spectrum obtained shows characteristic bands at 3436 cm$^{-1}$, 2979 cm$^{-1}$, 2932 cm$^{-1}$, 1721 cm$^{-1}$, 1638 cm$^{-1}$, 1454 cm$^{-1}$, 1320 cm$^{-1}$, 1297 cm$^{-1}$, 1176 cm$^{-1}$, 1013 cm$^{-1}$ and 943 cm$^{-1}$.

Proton magnetic resonance: chemical shifts at 6.1 ppm (m, 1H), 5.55 ppm (m, 1H), 4.45–4.05 ppm (m, 2H), 3.9–3.4 ppm (m, 2H), 3.5 ppm (m, 2H, O$\underline{H}$), 1.95 (m, 3H) and 1.18 (d, 8Hz, 3H).

Carbon 13 magnetic resonance: chemical shifts at 167.7 ppm ($\underline{C}$=O), 135.6 ppm (>$\underline{C}$=), 126.1 ppm ($\underline{C}H_2$=), 77.9 ppm ($\underline{C}H$—OH), 66.1 ppm ($\underline{C}$HOHCH$_3$), 65.3 ppm ($\underline{C}H_2$—O), 17.9 ppm ($\underline{C}H_3$), 17.5 ppm ($\underline{C}H_3$).

EXAMPLE 18

The operating method of Example 15 is repeated replacing epoxydicyclopentenyloxyethyl methacrylate by epoxydicyclopentenyloxyethyl acrylate. The reaction mixture is stirred for 3 days at ambient temperature. The diol of formula:

[Structure: acrylate ester linked through —O—CH$_2$—CH$_2$—O— to a bicyclic diol bearing two OH groups]

is recovered in a yield of 67%.

This product is characterized by:

Infrared spectroscopy: the spectrum obtained shows characteristic bands at 3397 cm$^{-1}$, 2955 cm$^{-1}$, 1727 cm$^{-1}$, 1637 cm$^{-1}$, 1619 cm$^{-1}$, 1407 cm$^{-1}$, 1195 cm$^{-1}$, 984 cm$^{-1}$ and 809 cm$^{-1}$.

Proton magnetic resonance: chemical shifts at 6.8–5.7 ppm (m, 3H), 4.4–3.2 ppm (m, 9H of which 2 O$\underline{H}$) and 2.5–1.1 ppm (m, 1 OH).

EXAMPLE 19

48 millimoles of sodium acetate and 50 ml of glacial acetic acid are placed in a reactor. A solution of 10 millimoles of glycidyl methacrylate in 5 ml of methylene chloride is added dropwise. The mixture obtained is stirred for 2 days at ambient temperature. At the end of this period, 20 ml of water are added and the aqueous phase is extracted with methylene chloride. The organic phase is washed with a saturated NaHCO$_3$ solution. After removal of the solvents, the organic reaction products are subjected to chromatography on a silica column, using eluents of increasing polarity: mixture of 85% of petroleum ether and 15% of ethyl acetate, then 50% of petroleum ether and 50% of ethyl acetate. The reaction leads to a mixture of acetate-alcohol isomers of formulae:

$$\underset{H_2C}{\overset{H_3C}{\diagdown}}C=\overset{O}{\overset{\|}{C}}-O-CH_2-\underset{OH}{\overset{|}{CH}}-\underset{OCOCH_3}{\overset{|}{CH_2}}$$

$$\underset{H_2C}{\overset{H_3C}{\diagdown}}C=\overset{O}{\overset{\|}{C}}-O-CH_2-\underset{OCOCH_3}{\overset{|}{CH}}-\underset{OH}{\overset{|}{CH_2}}$$

in a yield of 44%.

The 2-hydroxy-3-acetoxypropyl methacrylate was characterized by:

Infrared spectroscopy: the spectrum obtained shows characteristic bands at 3478 cm$^{-1}$, 2960 cm$^{-1}$, 1739 cm$^{-1}$, 1723 cm$^{-1}$, 1634 cm$^{-1}$, 1454 cm$^{-1}$, 1297 cm$^{-1}$, 1165 cm$^{-1}$ and 945 cm$^{-1}$.

Proton nuclear magnetic resonance: chemical shifts at 6.05 ppm (m, 1H), 5.5 ppm (m, 1H), 4.3–3.4 ppm (m, 6H of which 1 O$\underline{H}$), 2.0 ppm (m, 3H) and 1.9 ppm (m, 3H).

Carbon 13 nuclear magnetic resonance: chemical shifts at 170.6 ppm ($\underline{C}$=O), 166.7 ppm ($\underline{C}$=O), 135.4 ppm (>$\underline{C}$=), 125.7 ppm ($\underline{C}H_2$=), 67.2 ppm ($\underline{C}$HOH), 64.9 ppm (O$\underline{C}H_2$), 62.2 ppm ($\underline{C}H_2$OCO), 20.2 ppm ($\underline{C}H_3$CO) and 17.7 ppm ($\underline{C}H_3$).

EXAMPLE 20

20 millimoles of glycidyl methacrylate and 25.56 g of chloroform and 20.5 mg of triphenylphosphine are introduced into a reactor. 20 millimoles of trimethylsilane chloride are added to the solution obtained, keeping the temperature of the reaction mixture below 25° C. After 30 minutes, the solvent is evaporated and the organic compounds are subjected to chromatography on an alumina column, using eluents of increasing polarity: mixture of 95% of petroleum ether and 5% of ethyl acetate, then 70% of petroleum ether and 30% of ethyl acetate. The reaction leads to silylated chloro-ether, in a yield of 33%, and to chloro-alcohol, in a yield of 55%, the said compounds having the respective formulae:

$$\underset{H_2C}{\overset{H_3C}{\diagdown}}C=\overset{O}{\overset{\|}{C}}-O-CH_2-\underset{OSi(CH_3)_3}{\overset{|}{CH}}\overset{CH_2}{\underset{Cl}{\diagdown\diagup}}$$

and $$\underset{H_2C}{\overset{H_3C}{\diagdown}}C=\overset{O}{\overset{\|}{C}}-O-CH_2-\underset{Cl}{\overset{|}{CH}}-\underset{OSi(CH_3)_3}{\overset{|}{CH_2}}$$

$$\underset{H_2C}{\overset{H_3C}{\diagdown}}C=\overset{O}{\overset{\|}{C}}-O-CH_2-\underset{OH}{\overset{|}{CH}}-\underset{Cl}{\overset{|}{CH_2}}$$

and $$\underset{H_2C}{\overset{H_3C}{\diagdown}}C=\overset{O}{\overset{\|}{C}}-O-CH_2-\underset{Cl}{\overset{|}{CH}}-\underset{OH}{\overset{|}{CH_2}}$$

The silylated chloro-ethers are characterized by:

Infrared spectroscopy: the spectrum obtained shows characteristic bands at 2960 cm$^{-1}$, 1727 cm$^{-1}$, 1640

$cm^{-1}$, 1454 $cm^{-1}$, 1328 $cm^{-1}$, 1296 $cm^{-1}$, 1253 $cm^{-1}$ and 944 $cm^{-1}$.

Proton nuclear magnetic resonance: chemical shifts at 6.1 ppm (m, 1H), 5.55 ppm (m, 1H), 4.3-3.4 ppm (m, 5H), 2.0 ppm (m, 3H) and 0.2 ppm (s, 9H).

The chloro-alcohols are characterised by:

Proton nuclear magnetic resonance: chemical shifts at 6.1 ppm (m, 1H), 5.5 ppm (m, 1H), 4.3-3.4 ppm (m, 6H of which 1 O$\underline{H}$) and 2.0 ppm (m, 3H).

EXAMPLE 21

10 millimoles of glycidyl methacrylate and then 10 millimoles of boron trifluoride etherate containing 48% of freshly distilled $BF_3$ are introduced successively into a reactor which is kept at $-30°$ C. and contains 15 ml of methanol. This mixture is kept at $-30°$ C. for 2 hours, with stirring, and then at 25° C. for 12 hours. A mixture of the methacrylate isomers of formulae:

$$H_3C\diagdown \quad \underset{\|}{O}$$
$$\phantom{H_3}C-C-O-CH_2-CHOH-CH_2-OCH_3$$
$$H_2C\diagup$$

and $$H_3C\diagdown \quad \underset{\|}{O} \qquad \diagup OCH_3$$
$$\phantom{H_3}C-C-O-CH_2-CH$$
$$H_2C\diagup \phantom{XXXXXXXXXX} \diagdown CH_2OH$$

is then recovered, in a yield of 95% based on the glycidyl methacrylate.

2-hydroxy-3-methoxypropyl methacrylate was characterized by

Infrared spectrophotometry: the spectrum obtained (FIG. 7) shows characteristic bands at 3454, 2929, 1722, 1639, 1453, 1321, 1297 and 1171 $cm^{-1}$.

Carbon 13 and proton nuclear magnetic resonance: the chemical shifts expressed in ppm are indicated in Table III below.

EXAMPLE 22

The operating method of Example 21 is repeated replacing glycidyl methacrylate by crotyl methacrylate. A mixture of the methacrylate isomers of formulae $$H_3C\diagdown \quad \underset{\|}{O} \qquad \diagup OCH_3$$
$$\phantom{H_3}C-C-O-CH_2-CHOH-C$$
$$H_2C\diagup \phantom{XXXXXXXXXXX} \diagdown CH_3$$

and $$H_3C\diagdown \quad \underset{\|}{O} \qquad \diagup OCH_3$$
$$\phantom{H_3}C-C-O-CH_2-CH$$
$$H_2C\diagup \phantom{XXXXXXXXXX} \diagdown CHOH-CH_3$$

is recovered in a yield of 91%.

2-hydroxy-3-methoxybutyl methacrylate was characterized by:

Infrared spectrophotometry: the spectrum obtained (FIG. 8) shows characteristic bands at 3460, 2933, 1722, 1638, 1453, 1322, 1298 and 1170 $cm^{-1}$.

Carbon 13 and proton nuclear magnetic resonance: the chemical shifts expressed in ppm are indicated in Table III below.

EXAMPLE 23

The operating method of Example 21 is repeated replacing glycidyl methacrylate by epoxydicyclopentenyloxyethyl methacrylate. A mixture of methacrylate isomers of formula $$H_3C\diagdown \quad \underset{\|}{O}$$
$$\phantom{H_3}C-C-O-(CH_2)_2-O\text{--[dicyclopentenyl-OH, OCH}_3\text{]}$$
$$H_2C\diagup$$

is recovered in a yield of 90% and is characterized by:

Infrared spectrophotometry: the spectrum obtained (FIG. 9) shows characteristic bands at 3435, 2949, 1722, 1638, 1452, 1321, 1296 and 1168 $cm^{-1}$.

Carbon 13 and proton nuclear magnetic resonance: the chemical shifts expressed in ppm are indicated in Table III below.

TABLE III

| Example | 21 | 22 | 23 |
|---|---|---|---|
| $^{13}$C NMR | | | |
| δ (CO) | 166.9 | 167.4 | 166.9 |
| δ (C=) | 135.5 | 135.9 | 135.7 |
| δ ($CH_2$=) | 125.6 | 125.7 | 125.3 |
| δ ($CH_2$—O—$CH_3$) | 73.2 | 77.4 | 86.1-89.4 |
| δ (CHOH) | 67.9 | 71.6 | 76.3 |
| δ ($CH_2$—O) | 65.3 | 65.9 | 63.6-65.6-81.2 |
| δ ($OCH_3$) | 58.6 | 56.3 | 57.1-57.6 |
| δ ($CH_3$) | 17.8 | 14.2-18.0 | 17.8 |
| $^1$H NMR | | | |
| δ ($CH_2$=) | 6.1 (m,1H) | 6.05 (m,1H) | 6.1 (m,1H) |
|  | 5.5 (m,1H) | 5.55 (m,1H) | 5.5 (m,1H) |
| δ ($CH_2$) | 3.2-4.3 (m,8H,OH) | 3.1-4.2 (m,7H,OH) | 3.2-3.8 (m,8H,OH) |
| δ ($CH_3$) | 1.9 (m,3H) | 1.9 (m,3H) | 0.9-2.4 (m,13H) |
| δ ($CH_3$) | | 1.1 (m,3H) | |
| δ ($OCH_2$) | | | 4.1-4.4 (m,2H) |

EXAMPLE 24

The operating method of Example 21 is repeated replacing glycidyl methacrylate by epoxydicyclopentenyloxyethyl acrylate. A mixture of acrylate isomers of formula $$H_2C=CH-\underset{\|}{\overset{O}{C}}-O-(CH_2)_2-O\text{--[dicyclopentenyl-OH, OCH}_3\text{]}$$

is recovered in a yield of 92% and is characterized by:

Infrared spectrophotometry: the spectrum obtained (FIG. 10) shows characteristic bands at 3436, 2955, 1728, 1637, 1450, 1297 and 1194 $cm^{-1}$.

Carbon 13 and proton nuclear magnetic resonance: the chemical shifts expressed in ppm are indicated in Table IV below.

EXAMPLE 25

20 millimoles of glycidyl methacrylate, 40 millimoles of methyl ethyl ketone and 1.02 gram of an ion exchange resin, having a particle size of 20 to 50 mesh, marketed under the name AMBERLIST 15, are placed in a reactor. The mixture is stirred at 25° C. for 2 hours.

The reaction leads to the formation, in a yield of 40%, of dioxolane of formula

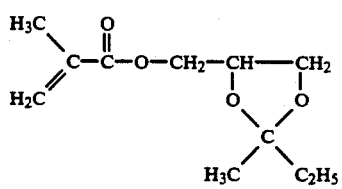

which is characterised by:

Infrared spectrophotometry: the spectrum obtained (FIG. 11) shows characteristic bands at 2982, 1724, 1639, 1453 and 1166 cm$^{-1}$.

Carbon 13 and proton nuclear magnetic resonance: the chemical shifts expressed in ppm are indicated in Table IV below.

EXAMPLE 26

The dioxolane obtained in Example 25 is placed in a reactor with 5 ml of 10% sulfuric acid and 10 ml of diethyl ether. The mixture is stirred at 25° C. for 14 hours. The reaction leads to the formation, in a yield of 25 of the diol of formula

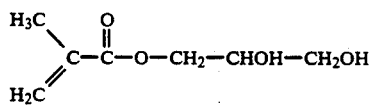

EXAMPLE 27

The operating method of Example 25 is repeated replacing glycidyl methacrylate by epoxycrotyl methacrylate. The reaction leads to the formation, in a yield of 43%, of dioxolane of formula

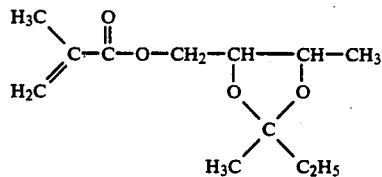

which is characterized by:

Infrared spectrophotometry: the spectrum obtained (FIG. 12) shows characteristic bands at 2982, 1723, 1639, 1453 and 1165 cm$^{-1}$.

Carbon 13 and proton nuclear magnetic resonance: the chemical shifts expressed in ppm are indicated in Table IV below.

EXAMPLE 28

The dioxolane obtained in Example 27 is subjected to the operating conditions of Example 26. The reaction leads to the formation, in a yield of 77%, of the diol of formula

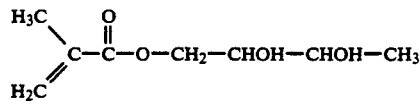

TABLE IV

| Example | 24 | 25 | 27 |
|---|---|---|---|
| $^{13}$C NMR | | | |
| δ (CO) | 165.1 | 166.4 | 166.2 |
| δ (CH$_2$=) | 130.1 | 125.4 | 125.3 |
| δ (C=) | 127.4 | 135.5 | 136.8 |
| δ (CHOCH$_3$) | 85.6–88.7 | | |
| δ (CH$_2$—O) | 63.0–65.0–81.5 | 64.0–73.6 | 62.8–77.8 |
| δ (CHOH) | 75.6 | | |
| δ (OCH$_3$) | 56.8 | | |
| δ (CH$_2$) | 28.9–49.9 | 31.1–32.0 | 29.3–33.0 |
| δ (C—O) | | 111.1 | 109.5–111.3 |
| δ (CH$_3$) | | 7.6–17.8–23.6 | 8–15–18–24 |
| $^1$H NMR | | | |
| δ (CH$_2$=) | 5.6–6.7(m,3H) | 6.0(m,1H) 5.5(m,1H) | 6.0(m,1H) 5.45(m,1H) |
| δ (OCH$_2$) | 4.0–4.4(m,2H) | 3.5–4.4(m,5H) | 3.5–4.5(m,4H) |
| δ (CH$_3$) | 3.1–3.8(m,8H) | 1.9(m,3H) | 1.9(m,3H) |
| δ (OH) | 2.7(m,1H,OH) | | |
| δ (CH$_2$) | 0.9–2.4(m,10H) | 0.7–1.8(m,8H) | 0.7–1.8(m,11H) |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The entire disclosures of all applications, patents and publications, cited above, and of corresponding application(s) France 90/80607, filed Jul. 6, 1990, are hereby incorporated by reference.

What is claimed is:

1. A process for opening the epoxide function of a (methacrylic epoxide of formula V:

wherein:

X is oxygen, sulfur, a —NH radical, —NR$^3$ in which R$^3$ is an alkyl group of 1 to 12 carbon atoms, or oxyalkylene —O—(CH$_2$)$_n$ in which n is an integer ranging from 3 to 16 inclusive, R$^1$ is a hydrogen or alkyl of 1 to 5 carbon atoms, and R$^4$ is a hydrocarbon chain comprising 2 to 20 carbon atoms, which is straight-chain or branched alkyl, monocyclic or polycyclic cycloalkyl, heterocycloalkyl, or alkylaryl, said hydrocarbon chain also comprising an oxirane group, said process comprising reacting said (meth)acrylic epoxide with at least one reactive compound selected from the group consisting of a strong inorganic acid, a boron trifluoride etherate complex, and acid salt in the presence of the corresponding acid, a halide of a trialkylsilane or trialkoxysilane, or a ketone in the presence of a cationic resin.

2. A process according to claim 1, the reactive compound being a strong inorganic acid, wherein the reaction takes place in the presence of water.

3. A process according to claim 1, the reactive compound being a boron trifluoride etherate complex, wherein the reaction takes place in the presence of a saturated alcohol having 1 to 4 carbon atoms and a stoichiometric amount of complex based on epoxide.

4. A process according to claim 1, the reactive compound being an acid salt, wherein said salt is used in excess in a ratio of 2 to 10 moles per mole of epoxide, the reaction being performed using the corresponding acid as solvent.

5. A process according to claim 1, the reactive compound being a trialkylsilane halide or trialkoxysilane halide, wherein said halide is used in a substantially stoichiometric amount, the reaction being carried out in the presence of a catalyst, such as a phosphine, and of at least one solvent, at a temperature of from 0° C. to 25° C.

6. A process according to claim 1, the reactive compound being a ketone, wherein the reaction takes place at a temperature of between 10° C. and 50° C. and in the presence of at least one cationic resin in an amount of 20 to 50% by weight relative to the (meth)acrylic epoxide.

7. A process according to claim 2, wherein the reaction temperature is +10° C. to +50° C.

8. A process according to claim 3, wherein the reaction temperature is −50° C. to +30° C.

9. A process according to claim 4, wherein the reaction temperature is +20° C. to +60° C.

10. A process for preparing a compound of the formula

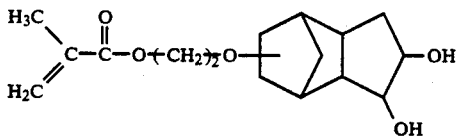

comprising reacting epoxydicyclophentenyloxyethyl methacrylate with sulfuric acid.

11. A process for preparing a compound of the formula

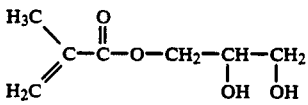

comprising reacting glycidyl methacrylate with sulfuric acid.

12. A process for preparing a compound of the formula

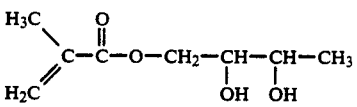

comprising reacting 2,3-epoxybutyl methacrylate with sulfuric acid.

13. A process for preparing a compound of the formula

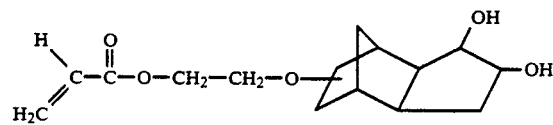

comprising reacting epoxydicyclopentenyloxyethyl acrylate with sulfuric acid.

* * * * *